(12) United States Patent
Chen et al.

(10) Patent No.: US 7,125,564 B2
(45) Date of Patent: Oct. 24, 2006

(54) WATER SOLUBLE AND PALATABLE COMPLEXES

(75) Inventors: Li-Lan H. Chen, Edison, NJ (US); Li Tao, Edison, NJ (US); Alfred Liang, Edison, NJ (US)

(73) Assignee: Lavipharm Laboratories, Inc., East Windsor, NJ (US)

( * ) Notice: Subject to any disclaimer, the term of this patent is extended or adjusted under 35 U.S.C. 154(b) by 19 days.

(21) Appl. No.: 10/071,380

(22) Filed: Feb. 8, 2002

(65) Prior Publication Data

US 2002/0147201 A1 Oct. 10, 2002

Related U.S. Application Data

(60) Provisional application No. 60/269,785, filed on Feb. 16, 2001.

(51) Int. Cl.
*A61K 9/14* (2006.01)

(52) U.S. Cl. ............................................. 424/489

(58) Field of Classification Search ............... None
See application file for complete search history.

(56) References Cited

U.S. PATENT DOCUMENTS

| | | | |
|---|---|---|---|
| 5,112,625 A | | 5/1992 | Zibell et al. |
| 5,576,014 A | * | 11/1996 | Mizumoto et al. .......... 424/435 |
| 6,103,765 A | | 8/2000 | Neal |
| 6,165,512 A | | 12/2000 | Mezaache et al. |
| 6,541,048 B1 | * | 4/2003 | Zyck et al. .................. 426/5 |

* cited by examiner

*Primary Examiner*—Michael P. Woodward
*Assistant Examiner*—Hasan S. Ahmed
(74) *Attorney, Agent, or Firm*—Lucas & Mercanti, LLP (57) ABSTRACT

The products and methods of the present invention provide a means for increasing the solubility and bioavailability of active agents. More particularly the invention provides compositions containing active agents as water-soluble complexes with glycyrrhizin, and methods of preparing such complexes. The invention further provides methods for the preparation of highly water soluble complex dosage forms.

12 Claims, 6 Drawing Sheets

Basic drug powder

Glycyrrhizin alcohol solution or gel with suitable amount of preservatives

Clear drug/glycyrrhizin solution with preservatives

Spray drying drug/glycyrrhizin dry powder

Figure 6

WATER SOLUBLE AND PALATABLE COMPLEXES

This Application claims benefit to a provisional application No. 60/269,785, filed on Feb. 16, 2001.

The present invention relates to water soluble and palatable complexes. The present invention also relates to methods of making water soluble and palatable complexes and compositions and drug dosage forms incorporating such complexes.

Bioavailability is the fraction or percentage of a dose that reaches the systemic circulation intact, when not directly injected into the circulation. Bioavailability is clinically important because pharmacological and toxic effects are proportional to both dose and bioavailability. When bioavailability is low, inter- and intra-subject variability in bioavailability are magnified, and incomplete bioavailability can become a great concern. Therefore, the major reason for trying to maximize bioavailability is to maximize pharmaceutical scientists' abilities to control the plasma concentration and the effects of drugs. Moreover, maximizing bioavailability contributes to increased cost-effectiveness.

A number of factors may contribute to the poor bioavailability of a drug. Poor bioavailability may be due to low solubility, degradation at the site of absorption, poor membrane permeation, and pre-systemic first-pass metabolism. Two of these factors important to the instant invention, include low solubility and high presystemic first-pass metabolism. These factors are discussed in more detail below.

Various strategies have been used to improve the aqueous solubility of poorly water-soluble drugs. These strategies include techniques using micronization, surfactant systems, co-solvents, alternate solid states, solid dispersions, and complexation.

The alteration of apparent solubility of a poorly water-soluble drug can be achieved through complexation. There are several types of complexes: ionically bonded, hydrogen-bonded and non-bonded complexes (S. Yalkowsky, Chapter 8 (pages 321–386): *Solubilization by Complexation in Solubility and Solubilization in Aqueous Media*, ACS, New York, 1999 and A. Martin etc. Chapter 13 (pages 314–351): *Complexation and protein binding in Physical Pharmacy*, Lea & Febiger, Philadelphia, 1983). The use of complexation in overcoming pharmaceutical solubility problems has several advantages. Among these is the reversibility of the interaction. Dissociation of the complex to the individual reactants can occur rapidly and spontaneously upon dilution and/or pH change. However, there are some limitations. The first one is the possibility of precipitation upon dilution. Also, the properties of the complexing agent such as its taste, odor, color or pharmacological effects can be unacceptable. Consequently, the choice of ligand can be primarily dictated by the patient's response rather than solely by the ability to produce the necessary alterations in solubility behavior. Another factor is that the apparent solubility increase gained through complexation can be an order of magnitude or less. (A. J. Repta, Chapter 4 (pages 135–157): *Alteration of apparent solubility through complexation in Solubilization techniques*, edited by G. Amidon and S. Yalkowsky, 1981).

Selecting a complexing agent depends on the structure of the drug. Unlike buffers, cosolvents, and surfactants, complexing agents generally cannot conform to the shape of the solute. The complexing agent must be capable of interacting with the solute in a very structurally specific manner in order to form the complex. In addition, the choice of complexing agent includes factors such as amount, cost, toxicity and taste. Often, the choice of ligand is also determined at least in part by the patient's subjective response to taste, odor, color and the like.

In addition to water solubility, bioavailability of the drug or other active agent may be influenced by "first-pass effects". The "first-pass effect" of drugs given orally refers to the process of drug degradation during a drug's transport from initial ingestion to circulation in the blood stream. Often discussed in terms of bioavailability, it is not uncommon for a drug that is administered to a patient orally to be given in a 5-fold or greater amount than ultimately necessary due to the degradation that occurs in the patient's body after intake. For example, the impact of the first-pass effect can be demonstrated with the case of the antihistamine terfenadine, wherein 99.5% of a tablet given by mouth is quickly changed to metabolites; hence, the bioavailability of terfenadine is approximately 0.5% (D. Garteiz et al., Arzneim.-Forsch., 1982; 32:1185–1190). As a further example, cyclosporin A, administered to organ transplant patients, has a median oral bioavailability of approximately 30% and a bioavailability range of approximately 8–92% among patients. Because of this large inter-individual variation in cyclosporin bioavailability, frequent monitoring of blood concentrations during therapy initiation is necessary.

Non-oral administration routes through sublingual, rectal and vaginal mucosae have been used to avoid the presystemic elimination encountered with oral administration routes. The bioavailability of many poorly water-soluble drugs, however, is limited by the dissolution rates of the drugs. These non-oral administration routes offer limited biological fluid to dissolve drugs rapidly for absorption. Consequently, such non-oral administration routes in the past have been limited to use with drugs having relatively high water solubility and high membrane permeability.

One active agent that exemplifies the problems associated with poor bioavailability is famotidine. Famotidine is a histamine $H_2$-receptor antagonist which has been proven to be highly effective and useful in the treatment of peptic ulcers due to its capability of inhibiting gastric secretion (acid concentration and volume) and reducing pepsin secretion (volume output). Famotidine, or N'(aminosulfonyl)-3-[[[2-[(diaminomethylene)amino]-4-thiazolyl]methyl]thio] propanimidamide, is a white to pale yellow crystalline powder with a molecular weight of 337 Dalton and pKa of 6.8. Famotidine is a weak base which is freely soluble in glacial acetic acid, very slightly soluble in water and insoluble in ethanol. Its intrinsic water solubility is 0.278 mg/mL. It also has a very poor lipophilicity.

After oral administration of famotidine, dose-related peak plasma concentration is achieved within 1 to 3.5 hours. Bioavailability of famotidine from the tablet formulation is only approximately 43%, and is unaffected by food. Famotidine is incompletely absorbed after oral administration, due to its low water solubility and poor lipophilicity.

$H_2$-receptor antagonists including famotidine seem well suited for on-demand treatment for reflux symptoms, due to the rapid onset of effect and a decreased likelihood of the development of tolerance. It is therefore, important in administering such $H_2$-receptor antagonists that they be released from their dosage form quickly so that their uptake can be hastened, and peak serum levels can be achieved relatively quickly. These requirements must, however, be balanced against the need for providing an acceptable tasting dosage form. Famotidine has a bitter taste that preferably should be masked. It has been difficult to date to find a dosage form which can satisfy all of the many, and sometimes conflicting requirements.

Alternative dosage forms have been disclosed for famotidine. In the past, effervescent formulations have been proven to provide more rapid absorption and almost immediate clinical effect. Several other convenient dosage forms, such as chewable tablets and wafers, that can be administered as needed without drinking water, have been developed. However, to mask its bitter taste, either micro-encapsulated or relatively large particle-sized famotidine is used in the formulations to eliminate or minimize its dissolution or solubility in the oral cavity. The dissolution rate of famotidine is thereby reduced for both dosage forms. New dosage forms that address the problem of low water solubility, on-demand release, with convenient dosage forms are therefore needed for famotidine.

Another drug that is limited by its low solubility and low bioavailability is sildenafil. Sildenafil (or 5-[-2-ethoxy-5-(4-methylpiperazin-1ylsulphonyl)phenyl]-1-methyl -3-n-propyl-1,6-dihydro-7H-pyrazolo[4,3-d]pyrimidine) (U.S. Pat. No. 5,250,534) is a selective cGMP phosphodiesterase inhibitor that is useful in the treatment of erectile dysfunction. Sildenafil citrate salt also has limited water solubility (3.5 mg/ml) with a molecular weight of 666.7 Dalton. When formulated as a regular film tablet the solubility of sildenafil citrate is still only around 6–8 mg/mL. Moreover, the low solubility of sildenafil base or citrate salt has limited its incorporation into novel, non-oral delivery systems.

Sildenafil citrate is rapidly absorbed after oral administration, with absolute bioavailability of about 40%. The low solubility and high presystemic elimination of sildenafil contributes to its low oral bioavailability. As is the case with famotidine, improved dosage forms of sildenafil that address its low bioavailaibility are also needed.

Buspirone is another agent that suffers from a very high first-pass metabolism. Buspirone, chemically: 8-[4-[4-(2-pyrimidinyl)1-piperazinyl]butyl]-8-azaspiro(4,5)-decane -7,9-dione (disclosed in U.S. Pat. No. 3,717,634) is a pharmaceutically active compound which has been found to be effective for the treatment of anxiety disorders and depression. However, buspirone shows a very high first pass metabolism, and only about 4% of a therapeutic dose will reach the systemic circulation unchanged after oral administration (Mayol et al., Clin Pharmacol. Ther., 37, 210, 1985). Great interindividual variations in buspirone absorption have also been observed as demonstrated by variations of the maximum plasma concentration of drug by up to 10-fold (Gammans et al., American J. Med., 80,Suppl. 3B, 41–51, 1986).

The biological half-life of buspirone is very short and variable in man, on an order of 2–11 hours (Mayol et al., Clin Pharmacol. Ther., 37, 210, 1985). These pharmacokinetic properties necessitate a rather frequent daily dosing regimen which would be expected to have a negative effect on patient compliance. Since buspirone is rapidly absorbed after an oral dose, high peak plasma values occur shortly after drug administration and these are associated with the occurrence of undesired or adverse events observed during the first days of treatment. These adverse effects can also seriously impact patient compliance due to resultant deliberate disruption of the drug therapy. As was the case with the above described agents, new dosage forms of buspirone are also needed to address the problems associated with its bioavailability.

Accordingly, there is a need for improved methods for increasing the solubility of poorly water-soluble drugs, such as famotidine and sildenafil. Additionally what is needed are improved methods for delivering active ingredients that avoid the high first pass metabolism that affects active ingredients such as sildenafil and buspirone. Any such methods should additionally be amenable to providing the active ingredients in a wide range of dosage forms to allow the maximum flexibility of treatment options. Finally, for any oral dosage forms using these methods, provisions for improving the palatability of bitter tasting drugs needs to be provided to improve patient compliance.

SUMMARY OF THE INVENTION

The present invention includes a composition having a pharmaceutically acceptable carrier and an active agent complexed with glycyrrhizin, wherein the active agent contains at least one nitrogen-containing moiety and wherein the composition is substantially free of uncomplexed active agent. The glycyrrhizin is preferably glycyrrhizinic acid, more preferably 18-alpha- or 18-beta-glycyrrhizinic acid. The glycyrrhizinic acid is preferably ionically complexed with the active agent. The active agent can be famotidine, buspirone, sildenafil, caffeine or loratadine. Preferably the mole ratio of glycyrrhizinic acid to active agent 1:1 to 1:3. The nitrogen containing moiety is preferably an acyclic or heterocyclic amine, amide, imine, imide or nitrile.

The active agent can be abortifacients, ACE inhibitors, adrenocorticotropic hormones, α-adrenergic agonists, α-adrenergic blockers, α-glucosidase inhibitors, anabolic steroids, narcotic analgesics, non-narcotic analgesics, anorexics, anthelmintics, antiallergics, antialopecials, antiamebics, antianginals, antiarrhythmics, antiarthritics, antiasthmatics, antibiotics, anticholinergics, anticonvulsants, antidepressants, antidiabetics, antidiarrheals, antidotes, antidyskinetics, antiemetics, antiestrogens, antifungals, antiglaucoma agents, antigout agents, antihistaminics, antihypertensives, nonsteroidal antiinflamatories, antimalarials, antimigraines, antineoplastics, antiparkinsonians, antipheochromocytoma agents, antipneumocystis, antiprostatic hyperplasia agent, antiprotozoals, antipruritics, antipsoriatics, antipsychotics, antipyretics, antirickettsials, antispasmodics, antithrombocythemics, antithrombotics, antitussives, antiulceratives, antivirals, anxiolytics, aromatase inhibitors, benzodiazepine antagonists, β-adrenergic antagonists, β-adrenergic blockers, bradycardic agents, bronchodilators, calcium channel blockers, carbonic anhydrase inhibitors, cardiotonics, choleretics, cholinergics, cholinesterase inhibitors, cholinesterase reactivators, CNS stimulants, cytoprotectants, decongestants, diuretics, dopamine receptor agonists, dopamine receptor antagonists, ectoparasiticdes, emetics, expectorants, fibrinogen receptor antagonists, gastric secretion inhibitors, gastroprokinetics, hemostatics, histamine $H_2$ receptor antagonists, immunomodulators, immunosuppressants, keratolytics, MAO inhibitors, mucolytics, muscle relaxants, mydriatics, narcotic antagonists, nootropics, oxytocics, potassium channel activators, respiratory stimulants, sedatives, hypnotics, serenics, serotonin receptor agonists, serotonin receptor antagonists, serotonin uptake inhibitors, thrombolytics, tocolytics, vasodilators, and vasoprotectants.

The present invention includes a pharmaceutical dosage form containing a composition of this invention. The dosage form can be one of a reconstituted powder, a soluble, edible film sachet, a liquid for oral or parenteral administration, an effervescent tablet, a chewable tablet, a mucosal surface-coating hydrocolloid film, a fast dissolving intraoral wafer, a troche, a lozenge, a nasal spray, a powder for inhalation, a mucoadhesive device for buccal, rectal or vaginal administration, a controlled release tablet and a capsule containing enteric microcapsules. The dosage form can also contain at least one agent selected from a water soluble polymer, a water insoluble polymer, an emulsifier, a plasticizer, a taste modifier, a coloring agent, a preservative, a permeation enhancer, a stabilizer, an inert filler, a binder, a thickening agent, a buffering agent, a lipid vehicle, a metabolism inhibitor and a glidant.

The present invention also includes a method for making a complex of a glycyrrhizin and an active agent by mixing an active agent and glycyrrhizin in an aqueous solvent. Preferably the aqueous solvent is water. The method can include the additional step of recovering the resulting complex. Preferably the complex is recovered by spray drying or freeze drying. Preferably the aqueous solvent can be a hydroalcoholic solvent, more preferably where the active agent is mixed with glycyrrhizin which is dispensed or dissolved in the hydroalcoholic solvent. The method can include the additional step of recovering the resulting complex, preferably by spray drying or freeze drying. Preferably the hydroalcoholic solvent has water and one or more of methanol, ethanol or isopropanol; more preferably the weight solvent of alcohol in the hydroalcoholic solvent is greater than 10% and less than 90%; still more preferably greater than 20% and less than 80%.

The present invention encompases a method of making the complex by mixing a mixture of glycyrrhizin and an active agent with an aqueous solvent. Preferably the aqueous solvent is water or a hydroalcoholic solvent. The hydroalcoholic solvent can contain water and one or more of methanol, ethanol or isopropanol. Preferably the weight percent of alcohol in the hydroalcoholic solvent is greater than 10% and less than 90%; preferably greater than 20% and less than 80%. the method can include the additional step of recovering the resulting complex, preferably by spray drying or freeze drying.

Another aspect of the present invention is a method for enhancing the water solubility of an active agent comprising forming a complex with glycyrrhizin wherein the active agent contains at least one nitrogen-containing moiety. Preferably the water solubility is at least five times greater than the uncomplexed active agent, more preferably at least ten times, still more preferably at least twenty times and yet more preferably at least fifty times.

The active agent can be abortifacients, ACE inhibitors, adrenocorticotropic hormones, α-adrenergic agonists, α-adrenergic blockers, α-glucosidase inhibitors, anabolic steroids, narcotic analgesics, non-narcotic analgesics, anorexics, anthelmintics, antiallergics, antialopecials, antiamebics, antianginals, antiarrhythmics, antiarthritics, antiasthmatics, antibiotics, anticholinergics, anticonvulsants, antidepressants, antidiabetics, antidiarrheals, antidotes, antidyskinetics, antiemetics, antiestrogens, antifungals, antiglaucoma agents, antigout agents, antihistaminics, antihypertensives, nonsteroidal antiinflamatories, antimalarials, antimigraines, antineoplastics, antiparkinsonians, antipheochromocytoma agents, antipneumocystis, antiprostatic hyperplasia agent, antiprotozoals, antipruritics, antipsoriatics, antipsychotics, antipyretics, antirickettsials, antispasmodics, antithrombocythemics, antithrombotics, antitussives, antiulceratives, antivirals, anxiolytics, aromatase inhibitors, benzodiazepine antagonists, β-adrenergic antagonists, β-adrenergic blockers, bradycardic agents, bronchodilators, calcium channel blockers, carbonic anhydrase inhibitors, cardiotonics, choleretics, cholinergics, cholinesterase inhibitors, cholinesterase reactivators, CNS stimulants, cytoprotectants, decongestants, diuretics, dopamine receptor agonists, dopamine receptor antagonists, ectoparasiticdes, emetics, expectorants, fibrinogen receptor antagonists, gastric secretion inhibitors, gastroprokinetics, hemostatics, histamine $H_2$ receptor antagonists, immunomodulators, immunosuppressants, keratolytics, MAO inhibitors, mucolytics, muscle relaxants, mydriatics, narcotic antagonists, nootropics, oxytocics, potassium channel activators, respiratory stimulants, sedatives, hypnotics, serenics, serotonin receptor agonists, serotonin receptor antagonists, serotonin uptake inhibitors, thrombolytics, tocolytics, vasodilators, and vasoprotectants.

GLOSSARY

The following terms will be used throughout:

"Active agent" or "active ingredient" means a drug, diagnostic agent, contrast agent, dye, immunoactive substance or other agent having a pharmacologic, biological or diagnostic effect or purpose.

"Bioavailability" as used herein is the percentage of dose that reaches the systemic circulation intact, when not directly injected into the circulation.

"Biologically acceptable" or "pharmaceutically acceptable" means a compound composition or salt which does not cause toxic or other unacceptable effects when administered to a human.

"Complex" means an entity comprising one or more molecules, ions or salts held together by ionic, hydrogen bonding or other noncovalent forces.

"Glycyrrhizin" means glycyrrhizin or glycyrrhizinic acid, any biologically acceptable salts and optical and geometric isomers of any of the foregoing.

"Highly water-soluble complex" means an active ingredient/glycyrrhizin complex wherein the water-solubility of the complex is at least five (5) fold greater than the active ingredient alone.

"Mucoadhesive" as used herein is a film or glycyrrizin dosage form that is capable of interacting with a mucous surface and being retained or held on the mucous surface for extended periods of time.

"Nitrogen-containing moiety" means a nitrogen containing group which can be protonated to form a cation or which can form hydrogen bond(s) with the glycyrrhizin.

"Poorly water soluble drug" means a bioactive agent that has a water solubility of less than 1 part in 30 parts of water. Examples of these poorly water soluble drugs include, but are not limited to, famotidine, sildenafil, buspirone, caffeine, allopurinol, amlodipine, amphotericin B, bromocriptine, cimetidine, cisapride, cisplatin, clarithromycin, clonazepam, diagepam, dobutamine, docetaxel, doxazosin, erhthromycin, famotidine, finasteride, glipizide, ketotifen, lamotrigine, lansoprazole, loperamide, loratidine, lorazepam, milrinone, morphine, nicergoline, nifedipine, nimodipine, nisoldipine, omeprazole, piroxicam, risperidone, ropinirole, saleterol, sertraline, sulpiride, tenoxicam, trandolapril, triamterene, triazolam, trimethoprim, and troglitazone.

"Substantially free of uncomplexed active agent" means less than ten percent (10%) of the uncomplexed active agent, preferably less than one percent (1%) of the uncomplexed active agent.

BRIEF DESCRIPTION OF THE DRAWING

There are shown in the drawings certain exemplary embodiments of the present invention as presently preferred. It should be understood that the present invention is not limited to the embodiments disclosed as examples, and is capable of variation within the spirit and scope of the appended claims.

In the drawings.

DETAILED DESCRIPTION

The products and methods of the present invention provide a means for increasing the solubility and bioavailability of active agents. More particularly the invention provides active agents as highly water-soluble complexes with glycyrrhizin, and methods of preparing such complexes. The invention further provides methods for the preparation of highly water soluble dosage forms, for example, nasal/pulmonary administrations, fast dissolving dosage forms for oral and intra oral applications, and mucoadhesive dosage forms that can be administered sublingually, vaginally, and/or rectally from the water-soluble glycyrrhizin complexes.

Glycyrrhizin

Figure 1:
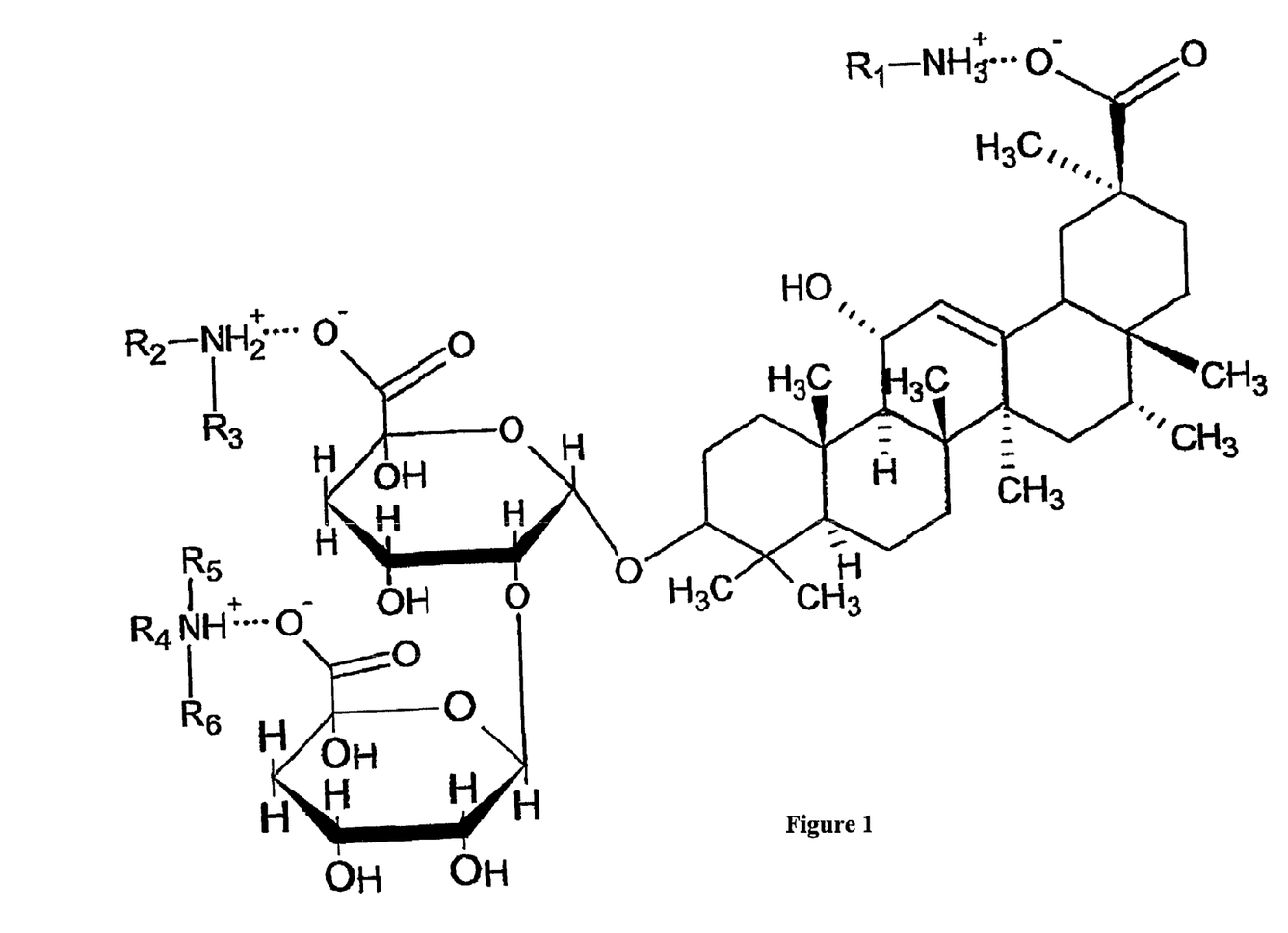
FIG. 1 illustrates three binding sites of an amine-glycyrrhizin ionic complex. The degree of substitution for the ammonium salts is arbitrary for this illustration.

The present invention relates to the use an anionic and palatable glycyrrhizin, to form complexes with poorly water-soluble basic agents. While not wishing to be bound by theory it is believed that the glycyrrhizin forms complexes with basic compounds through ionic bonds, hydrogen bonds, or both. Glycyrrhizin is water-soluble and exists as an anion that can be a potential ligand to form an ionically bonded complex with a cationic molecule active ingredient. One proposed embodiment for the glycyrrhizin complex with an amine containing compound is shown in FIG. 1. The resulting complexes can be considered as salts that have high water solubility (for example, ten fold or more than the active ingredient). These basic drugs include, for example, compounds that have nitrogen containing moieties such as acyclic or heterocyclic amines, amides, imines, imides and nitrites. An additional advantage is that the resulting complexes can mask or lessen the bitter taste of certain active agents. The complexes of the invention can be formulated into a wide variety of dosage forms or delivery systems to improve patient compliance, accelerate dissolution rate and increase bioavailability.

Glycyrrhizin is a naturally occurring GRAS (generally recognized as safe) flavoring agent found in licorice. Glycyrrhizin has been used as a taste-masking agent due to its unique sweetness and flavor perception. The sensory effects of glycyrrhizin can be attributed to their unusual temporal response. The effect is generally described as slow in onset, intense, sweet, and lasting. Glycyrrhizin can enhance flavors, modify sweetness perception, minimize bitterness, reduce metallic aftertaste, mask, unpleasant aftertaste, modify perceived mouthfeel and mimic glutamate effects. Its ability to form complexes with basic agents, and the realization that such complexes have improved water solubility, however, is unprecedented.

When glycyrrhizin has been used as a flavoring agent or sweetener, it is present in 0.01–0.2% by weight. In the present invention a complex form having different properties from either the glycyrrhizin or the active ingredients and the glycyrrhizin is generally present in about 100 times greater weight. Thus, the thermal properties of the active agent are changed as analyzed by differential scanning calorimetry. In addition, the Fourier transform infrared (FTIR) spectrum indicates that one or more functional groups have undergone some change in their vibrational states indicative of a chemical transformation or interaction. Furthermore, the solubility of the resulting complex is higher in water and aqueous alcohol than the active ingredient.

While glycyrrhizin has been used as a flavoring additive in foods and in the pharmaceutical industry for years, the present invention is directed to its use to form complexes with active ingredients to improve the solubility of poorly water soluble active ingredients. These glycyrrhizin complexes have been characterized by spectroscopic, chemical, and physical measurements. The active ingredient-glycyrrhizin complexes have surprisingly improved water solubilities. In one embodiment of the invention, optimized formulations of glycyrrhizin for specific basic drugs have been shown to improve their water-solubility. In some cases the water solubility of the drug is improved by over 50 fold.

As a consequence of their improved solubilities, the complexes can be conveniently incorporated into a wide variety of compositions and dosage forms. The dosage forms of the invention allow considerable flexibility in the treatment of patients. Owing to the wide range of available dosage forms of the invention, the optimized route of delivery can be tailored for a particular drug depending on its requirements for delivery. For example, some drugs require rapidly delivery to a patient's blood stream to reach the desired therapeutic effect. A highly water soluble complex and a fast releasing dosage form of the present invention provides these advantages. The pharmacokinetic limitations of particular drugs may also be overcome because of the wide variety of dosage forms of the invention. For example, water soluble dosage forms now provided by the invention can deliver a drug solution parenterally to avoid first-pass metabolism effects.

Figure 2:
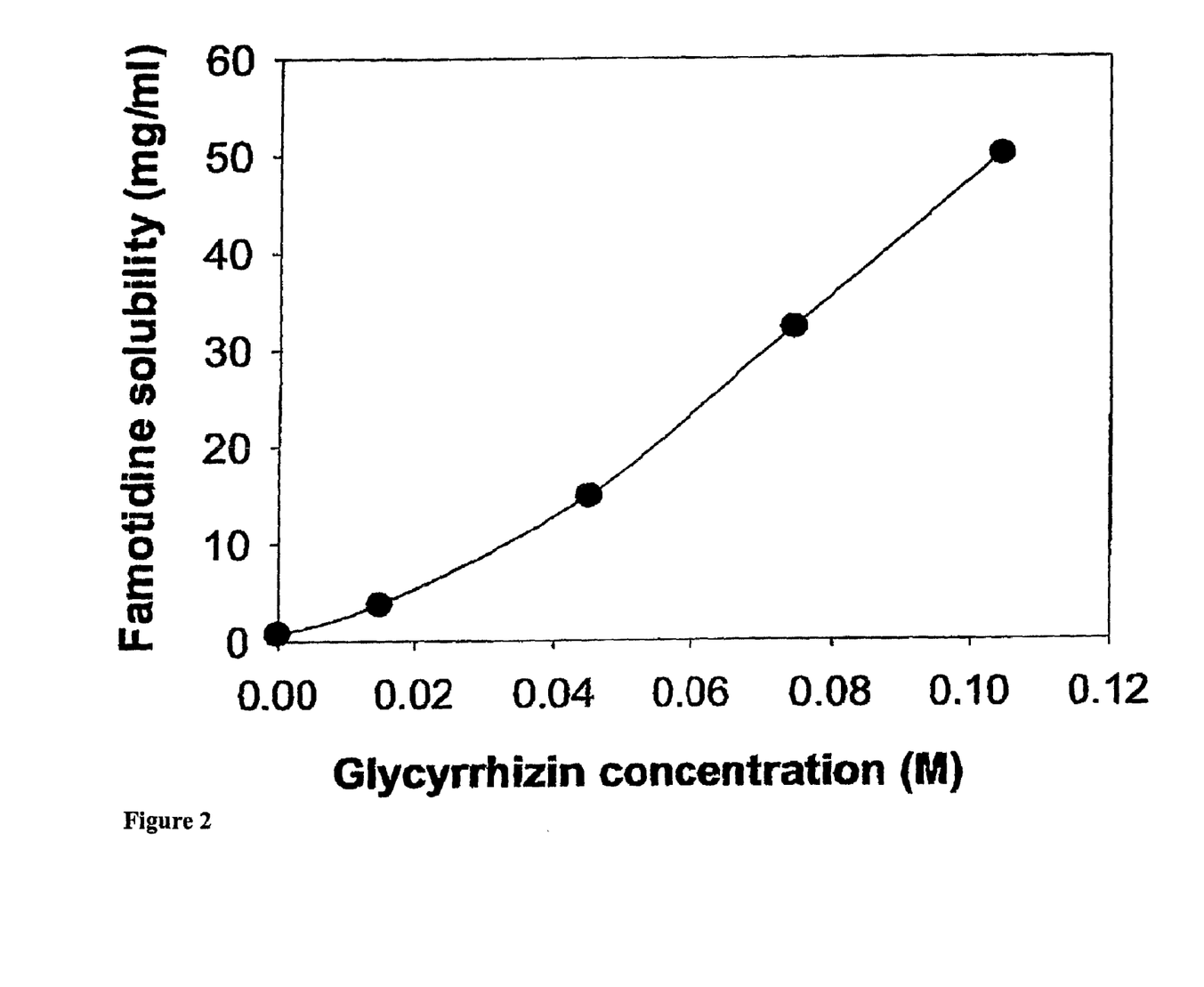
FIG. 2 is a graphical representation of the aqueous solubility of the famotidine/glycyrrhizin complex of the present invention.
Figure 3:
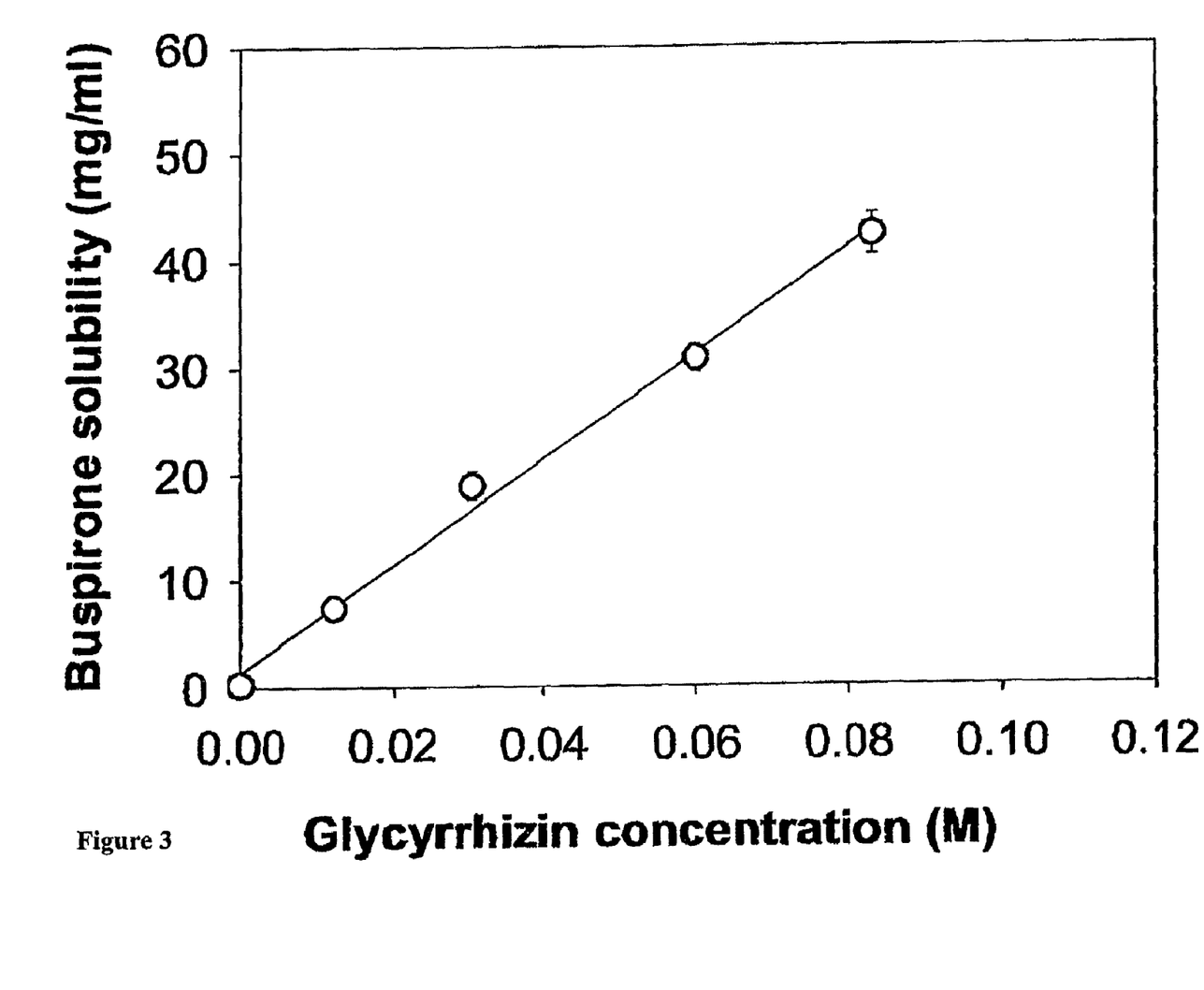
FIG. 3 is a graphical representation of the aqueous solubility of the buspirone/glycyrrhizin complex of the present invention.
Figure 4:
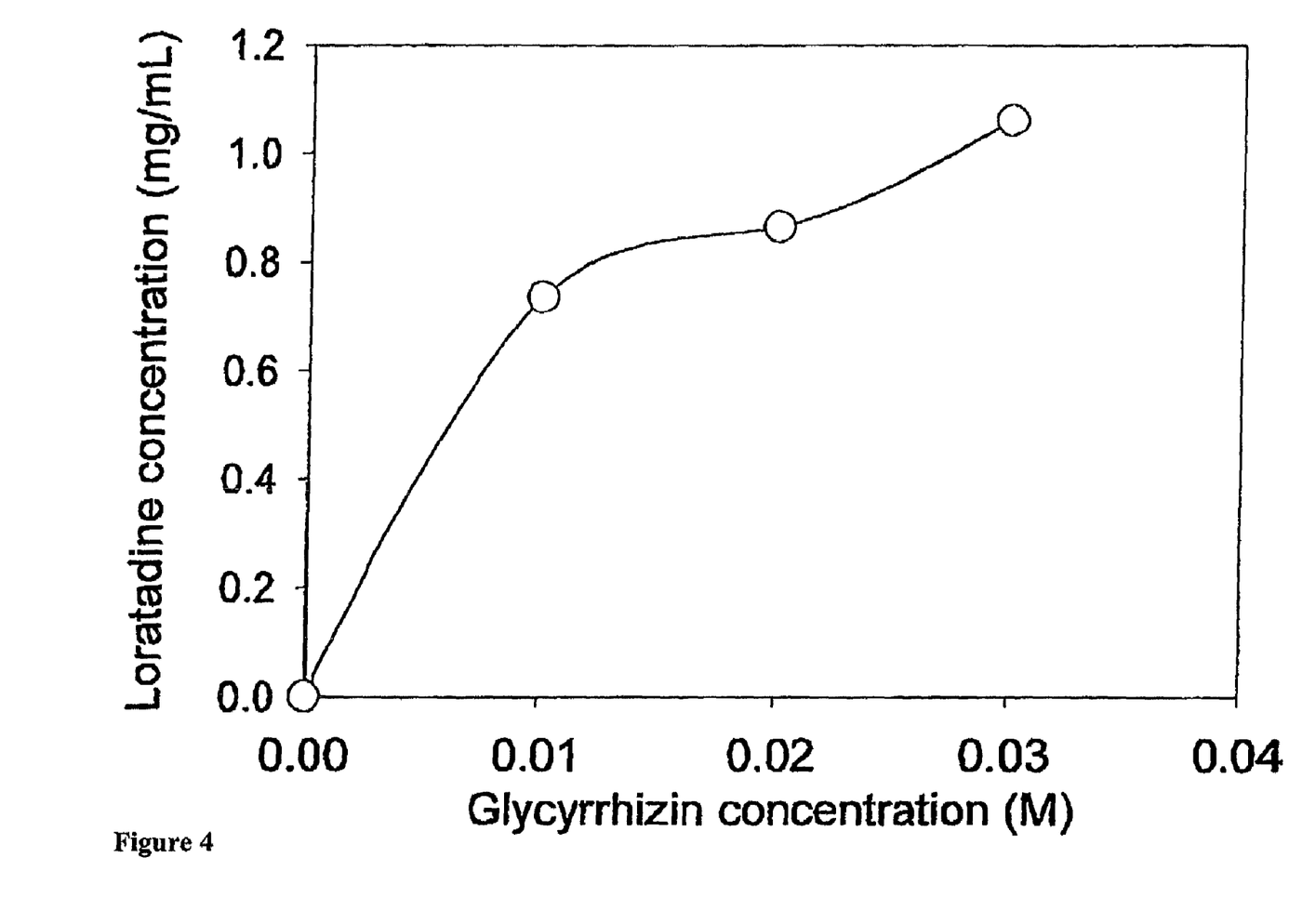
FIG. 4 is a graphical representation of the aqueous solubility of the loratadine/glycyrrhizin complex of the present invention.

The water-solubility of weakly basic active agents is dramatically improved through their incorporation into the glycyrrhizin complex. The solubility of famotidine, for example, is increased as it is incorporated into a complex with glycyrrhizin, as shown in the solubility phase diagram of FIG. 2. The saturated water solubility of famotidine alone is less than 1 mg/mL while the water solubility of the famotidine complex can reach as high as 50 mg/mL. Another poorly-water-soluble basic active agent, the anti-anxiety agent, buspirone, can also be rendered more water soluble through glycyrrhizin complexation. As graphically illustrated in FIG. 3, the water-solubility of buspirone was increased from 0.38 mg/mL, for buspirone alone, to 44 mg/mL through complexation with glycyrrhizin. FIG. 4 illustrates the solubility phase diagram of loratadine by adding glycyrrhizin. The solubilities of two other active agents, caffeine and sildenafil were also found to increase 6 and 200 fold, respectively, through complexation with glycyrrhizin.

In a preferred embodiment of the invention the famotidine/glycyrrhizin complex has a water solubility of at least 10 mg/mL, preferably at least 30 mg/mL. For buspirone, a preferred embodiment of the invention provides for a buspirone/glycyrrhizin complex with a solubility of at least 5 mg/mL, preferably at least 20 mg/mL. For sildenafil, in a preferred embodiment the solubility of its complex with glycyrrhizin is at least 2 mg/mL, preferably at least 10 mg/mL.

Figure 5:
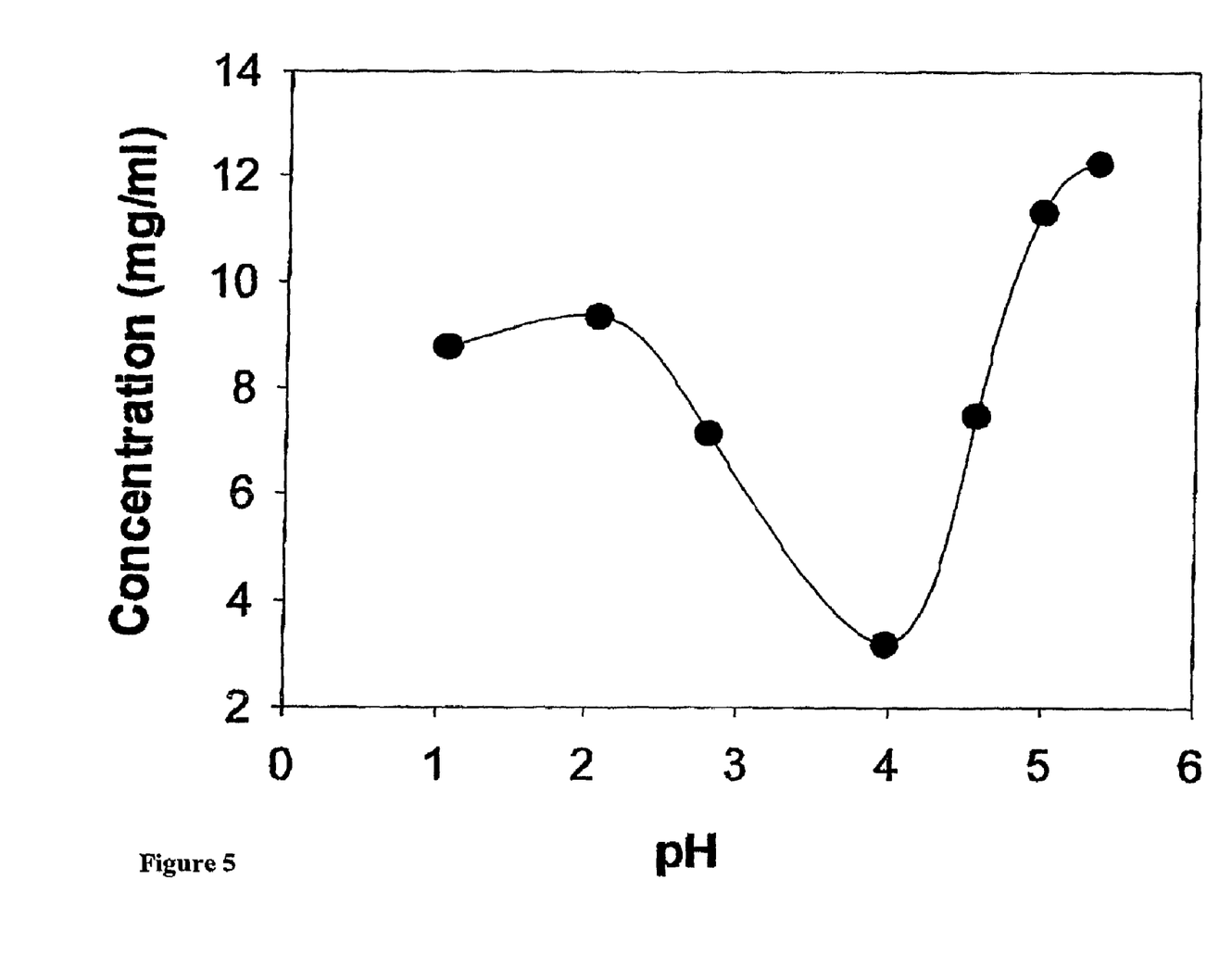
FIG. 5 is a graphical representation of pH on the famotidine/glycyrrhizin complex of present invention.

FIG. 5 shows the pH-reversibility of complexation of a famotidine-glycyrrhizin complex of the present invention. As the pH is reduced, the complex breaks apart into its constituents (glycyrrhizin and the poorly soluble famotidine). At still lower pH, the famotidine is protonated and becomes more water soluble. Thus, the complex is expected to dissociate in the stomach when orally ingested thereby releasing the famotidine so that there is no reduction in absorption.

Any active agent that has low water solubility and can form a complex with glycyrrhizin by accepting its proton(s) or forming hydrogen bond with the glycyrrhizin is suitable for the present invention. These active ingredients include, for example, compounds that contain moieties such as linear and heterocyclic amines, amides, imines, imides and nitriles. The present invention is applicable, but not limited to, drugs that are in the following therapeutic categories: abortifacients, ACE inhibitors (for example, lisinopril and quinapril), adrenocorticotropic hormones, alpha-adrenergic agonists (for example, phenylpropanolamine and pseudoephedrine), alpha-adrenergic blockers (for example, labetalol and terazosin), alpha-glucosidase inhibitors (for example, acarbose and miglitol), anabolic steroids (for example, pizotyline), narcotic analgesics (for example, codeine and dextromoramide), non-narcotic analgesics (for example, phenazopyridine and acetaminophen), anorexics (for example, fenfluramine and phentermine), anthelmintics (for example, quinacrine and mebendazole), antiallergics (for example, astemizole and azelastine), antialopecials (for example, finasteride and minoxodil), antiamebics (for example, chloroquine and chlortetracycline), antianginals (for example, acebutolol and gallopamil), antiarrhythmics (for example, amiodarone and penbutolol), antiarthritics (for example, hydroxychloroquine and chloroquine), antiasthmatics (for example, azelastine and ketotifen), antibiotics (for example, trimethoprim and neomycin B), anticholinergics (for example, poldine and procyclidine), anticonvulsants (for example, beclamide and carbamazepine), antidepressants (for example, clomipramine and dothiepin), antidiabetics (for example, glibornuride and glipizide), antidiarrheals (for example, defenoxin and diphenoxylate, antidotes (for example, neostigmine and tacrine), antidyskinetics (for example, amantadine and cabergoline), antiemetics (for example, buclizine and chlorpromazine), antiestrogens (for example, raloxifene and tamoxifen), antifungals (for example, terbinafine and nystatin), antiglaucoma agents (for example, betaxolol and carteolol), antigonadotropins (for example, danazol), antigout agents (for example, allopurinol and sulfinpyrazone), antihistaminics (for example, astemizole and azatadine), antihyperlipoproteinemics (for example, bezafibrate and colestipol), antihypertensives, (for example, acebutolol and indoramin), antihypothyroids (for example, liothyronine), nonsteroidal antiinflammatories (for example, indomethacin and piroxicam), antimalarials (for example, amodiaquine and halofantrine), antimigraines (for example, dolasetron and pizotyline), antineoplastics (for example, anastrozole and etoposide), anlparkinsonians (for example, amantadine and benserazide), antipheochromocytoma agents, antipneumocystis, antiprostatic hyperplasia agent, antiprotozoals (for example, amodiaquine and metronidazole), antipruritics (for example, cyproheptadiene), antipsoriatics (for example, methotrexate), antipsychotics (for example, benperidol and flupentixol), antipyretics (for example, acetaminophen), antirickettsials (for example, tetracycline), antispasmodics (for example, flavoxate and mebeverine), antithrombocythemics (for example, anagrelide), antithrombotics (for example, cilostazol and ticlopidine), antitussives (for example, dextromethorphan), antiuleeratives (for example, famotidine and omeprazole), antivirals (for example, amantadine and zidovudine), anxiolytics (for example, buspirone, lorazepam and medazepam), aromatase inhibitors (for example, aminoglutethimide and anastrozole), benzodiazepine antagonists, beta-adrenergic antagonists (for example, ephedrine and ritodrine), beta-adrenergic blockers (for example, acebutolol and atenolol), bradycardic agents, bronchodilators (for example, albuterol and ephedrine), calcium channel blockers (for example, amlodipine and flunarizine), carbonic anhydrase inhibitors (for example, dichlorphenamide), cardiotonics, choleretics, cholinergics (for example, neostigmine), cholinesterase inhibitors (for example, galanthamine), cholinesterase reactivators, CNS stimulants (for example, chlorphentermine and diethylpropion), cytoprotectants (for example, irsogladine), decongestants (for example, phenylpropanolamine), diuretics (for example, cimetidine and xipamide), dopamine receptor agonists (for example, quinagolide and ropinirole), dopamine receptor antagonists (for example, bromocriptine and ropinirole), ectoparasitiedes (for example, lufenuron), emetics, expectorants (for example, carbocysteine), fibrinogen receptor antagonists, gastric proton pump inhibitors (for example, lansoprazole), gastric secretion inhibitors (for example, omeprazole), gastroprokinetics (for example, cisapride), hemostatics, histamine $H_2$ receptor antagonists (for example, cimetidine), immunomodulators (for example, levamisole), immunosuppressants (for example, cyclophosphamide), keratolytics, leukotriene antagonists (for example, zafirlukast), miotics (for example, pilocarpine), MAO inhibitors (for example, selegiline and tranylcypromine), mucolytics (for example, carbocysteine and tasuldine), muscle relaxants (for example, flurazepam and mebeverine), mydriatics, narcotic antagonists (for example, naltrexone), nootropics (for example, bifemelane and idebenone), oxytocics (for example, ergonovine), potassium channel activators (for example, nicorandil), respiratory stimulants (for example, tacrine), sedatives and hypnotics (for example, chlordiazepoxide and clomethiazole), serenics (for example, eltoprazine), serotonic receptor agonists (for example, buspirone and methysergide), serotonic receptor antagonists (for example, granisetron and nefazodone), serotonin uptake inhibitors (for example, fluoxetine and sertraline), thrombolytics, tocolytics (for example, ritodrine), vasodilators (for example, flunarizine and oxprenolol), and vasoprotectants (for example, naftazone). Preferred drug substances include those intended for oral administration and transmucosal delivery where taste masking and/or solubility is a problem. The description of these therapeutic categories and a list of basic drugs can be found in DRUGS Synonyms & Properties, edited by G. W. A. Milne, Ashgate Publishing Company, England, 2000.

The therapy using these drugs preferably involves an on-demand release of the active agent. These on-demand active ingredients include, for instance, gastrointestinal, anti-emetics, anti-motion sickness, anti-allergy, anti-diarrheals and respiratory drugs. Gastrointestinal drugs, such as $H_2$-receptor antagonists famotidine, ranitidine and cimetidine can be used to treat the symptoms associated with peptic ulcers. Other examples include anti-diarrheals such as loperamide, anti-emetics such as granisetron and dimenhydramine and anti-allergy drugs such as loratadine.

Another preferable class of agents that are also on-demand agents include cyclic GMP phosphodiesterases such as sildenafil which is used to treat erectile dysfunction.

A molar ratio between active agent and glycyrrhizin ranging from 3:1 to 1:1 is preferred.

In addition to the active agent and glycyrrhizin that dosage forms may incorporate additional ingredients. These additional ingredients include, for example, preservatives, chelating agents, surfactants, taste modifiers, buffering agents, antacids, plasticizers, water soluble fillers, water insoluble fillers, binders, glidants, film forners, enteric coatings, solvents, coloring agents, thickening agents, osmotic agents, and semi-permeable membrane-forming agents.

Preservatives include anti-microbial agents and non-organic compounds are exemplified by sodium benzoate, parabens and derivatives, sorbic acid and its salts, propionic acids and its salts, sulfur dioxide and sulfites, acetic acid and acetates, nitrides and nitrates.

Chelating agents include edetic acid and its salts (disodium, tetrasodium, calcium disodium), diethylenetriaminepentaacetic acid and its salts (DTPA), hydroxyethylenediaminetriacetic acid and its salts (HEDTA) and nitilotriacetic acid (NTA). Preferably, the dosage forms of the present invention can general include 0 to 5% by weight of chelating agents.

Taste modifiers include flavoring agents, sweetening agents and taste masking agents and are exemplified by: the essential oils or water-soluble extracts of menthol, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum watermelon, nuts, durean, green tea, grapefruit, banana, butter, chamomile, sugar, dextrose, lactose, mannitol, sucrose, xylitol, maltitol, acesulfame potassium, talin, sucralose, aspartame, saccharin, sodium saccharin, sodium cyclamate, and honey. Preferably, the dosage forms of the present invention can include 0 to 10% taste modifiers on a weight basis.

Buffering agents include acidulants and alkalizing agents exemplified by citric acid, fumaric acid, lactic acid tartaric acid, malic acid, as well as sodium citrate, sodium bicarbonate, and carbonate, sodium or potassium phosphate, and magnesium oxide. Preferably, the dosage forms of the present invention can include 0 to 80% buffering agents on a weight basis.

Antacids include aluminum hydroxide, calcium carbonate, magnesium hydroxide, magnesium oxide, magnesium trisilicate, aluminum magnesium hydroxide and sodium bicarbonate. Preferably, the dosage forms of the present invention can include 0 to 50% antacids on a weight basis.

Plasticizers include glycerin, sorbitol, propylene glycol, polyethylene glycol, triacetin, triethyl citrate (TEC), acetyl triethyl citrate (ATEC) and other citrate esters. Preferably, the dosage forms of the present invention can include 0 to 40% plasticizers on a weight basis.

Fillers include microcrystalline cellulose, lactose, starch and derivatives, polyols (such as mannitol, sorbitol, xylitol), calcium phosphates and calcium sulfates. Preferably, the dosage forms of the present invention can include 0 to 70% fillers on a weight basis.

Binders include cellulose derivatives, povidone, polyvinylpyrrolidone, gelatin, natural gums and starch derivatives. Preferably, the dosage forms of the present invention can include 0 to 10% binders on a weight basis.

Glidants include talc, starch, alkali stearates, microcrystalline cellulose and colloidal silicon dioxide. Preferably, the dosage forms of the present invention can include 0 to 1% glidants on a weight basis.

Bioadhesive film formers include water soluble nonionic polymers such cellulose derivatives such as carboxymethylcellulose, hydroxyethyl cellulose, methylcellulose, hydroxypropyl cellulose and hydroxypropyl methylcellulose; polyvinylpyrrolidone; polyvinyl alcohol; polyethylene oxide; modified starch; gelatin; agar; locust bean gum; bentonite and scheroglucan; preferably polyvinylpyrrolidone, hydroxypropyl methylcellulose, hydroxypropyl cellulose, polyvinyl alcohol, gelatin, polyethylene oxide; most preferably, polyvinyl alcohol, gelatin and hydroxypropyl methylcellulose. Water soluble anionic polymers suitable for use with the present invention include, but are by no means limited to, polyacrylic acid such as carbopol, polycarbophil, poly(methyl vinyl ether-co-methacrylic acid), poly(2-hydroxyethyl methacrylate), poly(methylmethacrylate), poly (isobutylcyanoacrylate), poly(isohexycyanoacrylate) and polydimethylaminoethyl methacrylate; acacia; alginate; carrageenan; guar gum derivative; karaya gum; pectin; tragacanth gum; xanthan gum; dextran; sodium carboxymethylcellulose ("sodium CMC") and hyaluronic acid; preferably carbopol, polycarbophil, alginate, carrageenan, pectin and sodium CMC; most preferably carbopol, polycarbophil, alginate, carrageenan and sodium CMC. The anionic polymer or combination of anionic and noniomic polymers included in the bioadhesive, film preferably contains 10 to 60 wt % of an anionic polymer or combination of aniomic and nonionic polymers. Preferably, the dosage forms of the present invention can include 0 to 90% film formers on a weight basis.

Enteric coatings include methacrylic acid methacrylic acid ester copolymers (Eudragit), cellulose acetate phthlate, polyvinyl acetate phthalate, cellulose acetate trimellitate, carboxymethyl ethylcellulose and hydroxypropyl methylcellulose acetate succinate. Preferably, the dosage forms of the present invention can include 0 to 30% enteric coatings on a weight basis.

Solvents include water and ethanol. Preferably, the dosage forms of the present invention can include 0 to 80% solvents on a weight basis.

Coloring agents include FD&C coloring agents, natural coloring agents, and natural juice concentrates, pigments such as titanium oxide, silicon dioxide, and zinc oxide. Preferably, the dosage forms of the present invention can include 0 to 5% coloring agents on a weight basis.

Thickening agents include natural gums, cellulose derivatives, polyacrylic acid (Carbomer) and polyvinyl alcohol. Preferably, the dosage forms of the present invention can include 0 to 15% thickening agents on a weight basis.

Osmotic agents include simple eletrolytes (sodium chloride, potassium choride), water soluble sugars (fructose, sucrose, dextrose, sorbitol, xylitol) and polyglycols. Preferably, the dosage forms of the present invention can include 0 to 60% osmotic agents on a weight basis.

Semi-permeable, membrane-forming agents include polyvinyl alcohol, polyurethane, cellulose acetate, ethylcellulose and polyvinyl chloride. Preferably, the dosage forms of the present invention can include 0 to 30% semi-permeable, membrane-forming agents on a weight basis.

Emulsifying agents include solubilizers and wetting agents and are exemplified by polyvinyl alcohol, sorbitan esters, cyclodextrins, benzylbenzoate, glyceryl monostearate, polyoxyethylene alkyl ethers, polyoxyethylene stearates, poloxamer, polyoxyethylene castor oil derivatives, hydrogenated vegetable oils, bile salts, polysorbates and ethanol. Preferably, the dosage forms of the present invention can include 0 to 10% emulsifying agents on a weight basis.

Stabilizers include anti-oxidants, chelating agents, and enzyme inhibitors as exemplified by ascorbic acid, vitamin E, butylated hydroxyanisole (BHA), butylated hydroxytoluene (BHT), propyl gallate, dilauryl thiodipropionate, thiodipropionic acid, gum guaiac, citric acid, edetic acid and its salts and glutathione. Preferably, the dosage forms of the present invention can include 0 to 15% by weight of the stabilizers.

Figure 6:
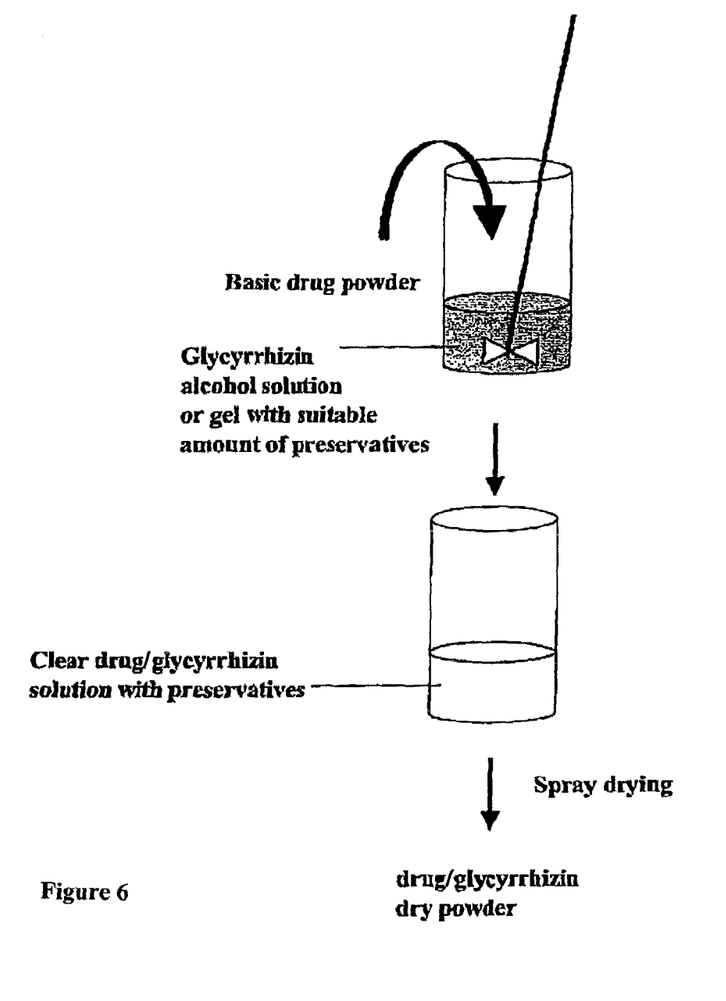
FIG. 6 depicts a method of preparing one dosage form, (a drug/glycyrrhizin complex powder) of the present invention.

The glycyrrhizin complexes can be prepared by any method that provides active agent/glycyrrhizin complexes with high water solubility. One embodiment is illustrated in FIG. 6. Glycyrrhizin is first dissolved or dispersed in an aqueous or hydroalcoholic solvent, preferably with suitable amounts of preservatives. The aqueous solvent is preferably water. The hydroalcoholic solvent includes water with a water soluble alcohol such as ethanol, methanol or isopropanol. Then, active agent, preferably as a powder, is gradually added into the glycyrrhizin solution or gel under agitation to result in a clear complex solution. The resulting complex solution can then be spray-dried or spray-coated with enteric polymers. The resulted complex powders are palatable (licorice-flavored), hygroscopic and highly water-soluble.

The resulted complexes can be formulated into various delivery systems to improve patient compliance, increase dissolution rate and control release rate. Preferred delivery systems include all oral dosage forms, nasal spray and inhalation. The oral dosage forms are palatable with high water solubility, fast dissolution and rapid absorption. These delivery systems include re-constituted powders packed in soluble and edible film sachets, solution for oral and/or parenteral administration, re-constituted enteric microcapsules for suspensions, troches, lozenges, effervescent tablets, chewable tablets, intraoral fast-dissolving films, fast-dissolving intraoral wafers, nasal liquid spray, nasal powder spray, inhalation powder, mucoadhesive devices for buccal, rectal and vaginal administration, osmotic tablets and capsules containing enteric microcapsules.

In another embodiment the invention relates to methods of treating diseases by administering a dosage form containing a highly water-soluble complex of an active agent and glycyrrhizin. More particularly what is provided is a method for treating an individual with an ulcer by administering a dosage form containing a highly water-soluble drug complex of an $H_2$ receptor antagonist and glycyrrhizin. A preferred method for treating an ulcer uses famotidine as the $H_2$-receptor antagonist in the dosage form of the invention. A more preferred method includes a method of treating an individual wherein the ratio of famotidine to glycyrrhizin on a molar basis is 3:1 to 1:1. The dosage forms administered to the individual include, for instance, tablets (including chewable tablets), effervescent tablets, lingual films and fast-dissolving tablets.

Also provided is a method of treating sexual dysfunction by administering a dosage form containing a drug complex of sildenafil and glycyrrhizin to an individual.

The present inventions include a method of treating seasonal allergy by administering a dosage form containing a complex of loratadine and glycyrrhizin to an individual.

Further provided is a method of treating anxiety by administering a dosage form containing a drug complex of buspirone and glycyrrhizin to an individual.

The dose of the dosage form or composition of the present invention as an active agent will be determined by the physician based on the weight, age and physical condition of the patient. In general, the dose of the composition or dosage form of the present invention will be equal to or less than the standard dose of the free active agent.

EXAMPLES

Some preferred embodiments of the present invention will now be further described through the following examples set forth hereinbelow which are intended to be illustrative of the preferred embodiments of the present invention and are not intended to limit the scope of the invention as set forth in the appended claims.

Example 1

Re-constituted Powders Packed in Soluble and Edible Film Sachet 27 grams of monoammonium glycyrrhizin and 33 grams of famotidine were dissolved in 1140 grams of 50% ethanol-water mixture. The resulting solution was then spray-dried to obtain famotidine/glycyrrhizin complex powder. 30 grams of complex powder was blended with 1 gram of cherry flavor powder, 1 gram of acesulfame potassium and 44 grams of sorbitol. The resulted powder, 92 mg as a unit weight, was filled in the water soluble and edible film sachet which is made from 10 mg of propylene glycol and 50 mg of HPMC with 2 mil thickness. The resulted sachet, which contains 20 mg of Famotidine, could be directly dropped into water to reconstitute aqueous solution or taken orally with or without drinking any water.

Example 2

Solution Dosage Form 13.1 grams of monoammonium glycyrrhizin and 6.1 grams of famotidine were dissolved in 138.8 grams of water. The resulting solution was then spray-dried to obtain famotidine/glycyrrhizin complex powder. 0.6 grams of the complex powder was dissolved in 65.85 grams of water, 0.02 grams of Nipagin M/Nipasol M(methylparaben/propylparaben, weight ratio 4:1), 0.02 grams of sodium ethylenediaminetetraacetic acid (EDTA), 0.01 grams of Cremaphor RH40 polydyoxyethylated castor oil, 0.5 grams of Cherry ice, 1 gram of acesulfame potassium, 30 grams of sorbitol, and 2 grams of polyvinylpyrrolidone were added into the solution and resulted in a homogenous solution. The final solution contains 0.2% (w/w) famotidine.

Example 3

Re-constituted Enteric Microcapsules for Suspensions 54 grams of monoammonium glycyrrhizin and 66 grams of famotidine were dissolved in 2280 grams of 50% ethanol-water mixture. 40 grams of cellulose acetate phthalate and 0.4 gram of propylene glycol was dissolved in 2359.6 grams of 1:1 acetone/ethanol. The complex solution was spray-dried and counter-spray-coated with the cellulose acetate phthalate solution to obtain enteric coated famotidine/glycyrrhizin complex microparticles. The core to shell ratio is 3:1. 80 grams of microparticles were well blended with 1 gram of acesulfame potassium, 1 gram of cherry flavor powder and 18 grams of sorbitol. The resulted powder, 120 mg, was packed into a unit pouch. Each pouch contains 40 mg famotidine.

Example 4

Effervescent Tablets 27 grams of monoammonium glycyrrhizin and 33 grams of famotidine were dissolved in 1140 grams of 50% ethanol-water mixture. The resulting solution was then spray-dried to obtain famotidine/glycyrrhizin complex powder. 20 grams of the complex powder was well blended with 1 gram of cherry flavor powder, 1 gram of acesulfame potassium, 39.7 grams of citric acid, 30.3 grams of sodium bicarbonate, 5 grams of mannitol, 2 grams of Methocel E5 (hydroxypropyl methylcellulose) and 1 gram of talc. The resulted powder was directly compressed into tablets with a unit weight of 180 mg. Each tablet contains 20 mg Famotidine.

Example 5

Chewable Tablets 27 grams of monoammonium glycyrrhizin and 33 grains of famotidine were dissolved in 1140 grams of 50% ethanol-water mixture. The resulting solution was then spray-dried to obtain famotidine/glycyrrhizin complex powder. 30 grams of the complex powder was well blended with 1 gram of cherry flavor powder, 1 gram of acesulfame potassium, 50 grams of mannitol, 13 grams of microcrystalline cellulose, 4 grams of Methocel E5 and 1 gram of talc. The resulted powder mixture was directly compressed into tablets with a unit weight of 120 mg. Each tablet contains 20 mg of famotidine.

Example 6

Intraoral Fast Dissolving Film 67.5 grams of monoammonium glycyrrhizin and 82.5 grams of famotidine were dissolved in 2350 grams of 50% ethanol-water mixture. The resulting solution was then spray-dried to obtain famotidine/glycyrrhizin complex powder. 6 grams of the complex powder, 0.01 gram of Nipagin M/Nipasol M, 0.015 gram of sodium EDTA, 1 gram of propylene glycol, 0.5 gram of peppermint oil and 3 grams of Methocel E15 were dissolved in 35 grams of 50% ethanol-water mixture to form homogenous and viscous solution for coating. The coating solution was casted at 20 mil and dried at 40° C. to remove water and ethanol. The resulted dry film with an estimated 2% of residual water was cut to suitable size and shape for unit dose pouching. the film weight ranges from 32 to 35 mg. Each film contains 10 mg Famotidine.

Example 7

Fast Dissolving Intraoral Wafer 80 grams of monoammonium glycyrrhizin and 40 grams of famotidine were dissolved in 1080 grams of water. The resulting solution was then spray-dried to obtain famotidine/glycyrrhizin complex powder. 60 grams of the complex powder, 0.1 gram of Nipagin M/Nipasol M, 0.1 gram of sodium EDTA, 1 gram of propylene glycol, 1.4 gram of peppermint flavor, 1.4 gram of acesulfame potassium, 24 grams of mannitol, and 12 grams of Methocel E5 were dissolved in 500 grams of water. The resulted homogenous solution was dispersed into molded blister packaging sheet for freeze drying process to remove water and result in fast dissolving intraoral wafer. The unit weight is 50 mg. Each wafer contains 10 mg famotidine.

Example 8

Osmotic Tablets 80 grams of monoammonium glycyrrhizin and 40 grams of famotidine were dissolved in 1080 grams of water. The resulting solution was then spray-dried to obtain famotidine/glycyrrhizin complex powder. 30 grams of the complex powder was well blended with 10 grams of sodium bicarbonate, 3 grams of Methocel E5, 1 gram of talc and 50 grams of potassium chloride. The resulted powder was directly compressed into osmotic cores. A suspension of micronized lactose/cellulose acetate/triethyl citrate in a weight ration of 2/2/1 in ethanol/dichloromethane in a weight ratio of 10.5/31.5 was prepared and sprayed onto the tablet cores in a pan coater. A laser was used to drill the release orifice of coated tablet. Each tablet, 200 mg, contains 20 mg famotidine.

Example 9

Capsules Containing Enteric Microcapsules 54 grams of monoammonium glycyrrhizin and 66 grams of famotidine were dissolved in 2280 grams of 50% ethanol-water mixture. 40 grams of cellulose acetate phthalate and 0.4 gram of propylene glycol was dissolved in 2359.6 grams of 1:1 acetone/ethanol. The complex was spray-dried and counter-spray-coated with the cellulose acetate phthalate solution to obtain enteric coated famotidine/glycyrrhizin complex microparticles. The core to shell ratio is 3.1. 40 grams of the resulted complex microparticles were then well blended with 30 grams of calcium carbonate, 19 grams of microcrystalline cellulose, and 1 gram of talc. The resulted powder mixture, 220 mg, was filled into a hard gelatin capsule. Each capsule contains 40 mg famotidine.

Example 10

Glycyrrhizin-Famotidine Complex; Solubility Improvement 10 ml of glycyrrhizin ammonium solution/dispersion, concentration ranged from 0.015 M to 0.1 M, were prepared using distilled water in 20 ml scintillation vials. 750 mg of Famotidine was added into each vial. The control study was conducted with zero concentration of glycyrrhizin. Four studied solutions and the control were mounted on a vertical rotator with a rotation speed of 10 rpm under room temperature for 24 hours. The supernatant of each vial was taken using a 5 ml syringe and filtered through a 0.45 um syringe filter. Discarded first three drops and collected 1 ml of filtrate in HPLC vial. Diluted each filtrate, 1/10 or 1/100, with distilled water. Diluted filtrates were analyzed by HPLC. The resulted concentration, mg/ml, is plotted as FIG. 2.

Example 11

Glycyrrhizin-Buspirone Complex; Solubility Improvement 10 ml of glycyrrhizin ammonium solution/dispersion, concentration ranged from 0.012 M to 0.083 M, were prepared using distilled water in 20 ml scintillation vials. 500 mg of Buspirone base was added into each vial. The control study was conducted with zero concentration of glycyrrhizin. Four studied solutions and the control were mounted on a vertical rotator with a rotation speed of 10 rpm under room temperature for 24 hours. The supernatant of each vial was taken using a 5 ml syringe and filtered through a 0.22 um syringe filter. Discarded first three drops and collected 1 ml of filtrate in HPLC vial. Diluted each filtrate, 1/10 or 1/100, with distilled water. Diluted filtrates were analyzed by HPLC. The resulted concentration, mg/ml, is plotted as a FIG. 3.

Example 12

Glycyrrhizin-Famotidine Complex; Reversibility 20 ml of glycyrrhizin/famotidine complex solution (12 mg/ml) was prepared. The solution pH was measured using Orion pH meter while 0.1 NHCl was gradually added into the solution drop-by-drop under stirring condition. During titration, 1 ml sample was taken, filtered, diluted and analyzed at pHs 5.35, 4.5, 4.0, 2.8, 2.0 and 1.0. The results are plotted as FIG. 5.

Example 13

Glycyrrhizin-Loratadine Complex; Solubility Improvement 10 ml of glycyrrhizin ammonium solution/dispersion, concentration ranged from 0.01 M to 0.03 M, were prepared using distilled water in 20 ml scintillation vials. 50 mg of Loratadine was added into each vial. The control study was conducted with zero concentration of glycyrrhizin. Three studied solutions and the control were mounted on a vertical rotator with a rotation speed of 10 rpm under room temperature for 24 hours. The supernatant of each vial was taken using a 5 ml syringe and filtered through a 0.22 um syringe filter. Discarded first three drops and collected 1 ml of filtrate in HPLC vial. Diluted each filtrate, 1/10 or 1/100, with distilled water. Diluted filtrates were analyzed by HPLC. The resulted concentration, mg/ml, is plotted as FIG. 4.

Example 14

Glycyrrhizin-Sildenafil Complex; Solubility Improvement 10 ml of 0.1 M glycyrrhizin ammonium solution/dispersion was prepared using distilled water in 20 ml scintillation vials. 500 mg of sildenafil base was added into each vial. The control study was conducted with zero concentration of glycyrrhizin. Studied solution and the control were mounted on a vertical rotator with a ration speed of 10 rpm under room temperature for 24 hours. The supernatant of each vial was taken using a 5 ml syringe and filtered through a 0.45 μm syringe filter. Discarded first three drops and collected 1 ml of filtrate in HPLC vial. Diluted each filtrate, 1/10 or 1/100 with distilled water. Diluted filtrates were analyzed by HPLC. The solubility of sildenfil was improved more than 200 fold.

Example 15

Glycyrrhizin-Caffeine Complex; Solubility Improvement 10 ml fo 0.1 M glycyrrhizin ammonium solution/dispersion was prepraed using distilled water in 20 ml scintillation vials. 500 mg of caffeine base was added into each vial. The control study was conducted with zero concentration of glycyrrhizin. Studied solution and the control were mounted on a vertical rotator with a ration speed of 10 rpm under room temperature for 24 hours. The supernatant of each vial was taken using a 5 ml syringe and filtered through a 0.45 μm syringe filter. Discarded first three drops and collected 1 ml of filtrate in HPLC vial. Diluted each filtrate, 1/10 or 1/100 with distilled water. Diluted filtrates were analyzed by HPLC. The solubility of caffeine was improved more than 5 fold.

The present invention having been disclosed in connection with the foregoing embodiments, additional embodiments will now be apparent to persons skilled in the art. The present invention is not intended to be limited to the embodiments specifically mentioned, and accordingly reference should be made to the appended claims rather than the foregoing discussion, to assess the spirit and scope of the present invention in which exclusive rights are claimed.

We claim:

1. A composition comprising a pharmaceutically acceptable carrier and an active agent complexed with glycyrrhizin, wherein the active agent contains at least one nitrogen-containing moiety, and wherein the composition is substantially free of uncomplexed active agent.

2. The composition according to claim 1, wherein the glycyrrhizin is selected from the group consisting of glycyrrhizin acid and its biologically acceptable salts.

3. The composition according to claim 2, wherein the glycyrrhizinic acid is an 18-alpha glycyrrhizinic acid or 18-beta-glycyrrhizinic acid.

4. The composition according to claim 2, wherein the glycyrrhizinic acid is ionically complexed with the active agent.

5. The composition according to claim 2, wherein the active agent is famotidine.

6. The composition according to claim 2, wherein the mole ratio of glycyrrbizinic acid to active agent is 1:1 to 1:3.

7. The composition according to claim 1, wherein the mole ratio of glycyrrhizin to active agent is 1:1 to 1:3.

8. The composition according to claim 1, wherein the nitrogen containing moiety is one or more of an acyclic or heterocycic amine, amide, imine, imide and nitrile.

9. The composition according to claim 1, wherein the active agent comprises abortifacients, ACE inhibitors, adrenocorticotropic hormones, α-adrenergic agonists, α-adrenergnic blockers, α-glucosidase inhibitors, anabotic steroids, narcotic analgesics, non-narcotic analgesics, anorexics, anthelmintics, antiallergics, antialopecials, antianiebics, antianginals, antiarrhytbmics, antiartbritics, antiasthmatics, antibiotics, anticholinergics, anticonvulsants, antidepressants, antidiabetics, antidiarrheals, antidotes, antidyskinetics, antiemetics, antiestrogens, antifungals, antiglaucoma agents, antigout agents, antihistaminics, antihypertensives, nonsteroidal antiinflamatories, antimalarials, antimigraines, antineoplastics, antiparkinsonians, antipheochromocytoma agents, antipneumocystis agents, antiprostatic hyperplasia agents, antiprotozoals, antipruritics, antipsoriatics, antipsychotics, antipyretics, antirickettsials, antispasmodics, antithrombocythemics, antithrombotics, antitussives, antiulceratives, antivirals, anxiolytics, aromatase inhibitors, benzodiazepine antagonists, β-adrenergic antagonists, β-adrenergic blockers, bradycardic agents, bronchodilators, calcium channel blockers, carbonic anhydrase inhibitors, cardiotonics, choleretics, cholinergics, cholinesterase inhibitors, cholinesterase reactivators, CNS stimulants, cytoprotectants, decongestants, diuretics, dopamine receptor agonists, dopamine receptor antagonists, ectoraraciticides, emetics, expectorants, fibrinogen receptor antagonists, gastric secretion inhibitors, gastroprokinetics, hemostatics, histamine $H_2$ receptor antagonists, immunomodulators, immunosuppressants, keratolytics, MAO inhibitors, mucolytics, muscle relaxants, mydriatics, narcotic antagonists, nootropics, oxytocics, potassium channel activators, respiratory stimulants, sedatives, hypnotics, serenics, serotonin receptor agonists, serotonin receptor antagonists, serotonin uptake inhibitors, thrombolytics, tocolytics, vasodilators, and vasoprotectants.

10. A pharmaceutical dosage form comprising the composition of claim 1.

11. The dosage form of claim 10, wherein the dosage form is selected from the group consisting of a reconstituted powder, a soluble, and edible film sachet, a liquidfor oral or parenteral administration, an effervescent tablet, a chewable tablet, a mucosal surface-coating hydrocolloid film, a fast dissolving intraoral wafer, a troche, a lozenge, a nasal spray, a powder for inhalation, a mucoadhesive device for buccal, rectal or vaginal administration, a controlled release tablet and a capsule containing enteric microcapsules.

12. The dosage form of claim 10, wherein the dosage form further comprises at least one reagent selected from the group consisting of a water soluble polymer, a water insoluble polymer, an emulsifier, a plasticizer, a taste modifier, a coloring agent, a preservative, a permeation enhancer, a stabilizer, an inert filler, a binder, a thickening agent, a buffering agent, a lipid vehicle, a metabolism inhibitor and a glidant.

* * * * *